United States Patent [19]

Gutman

[11] 4,219,547

[45] Aug. 26, 1980

[54] PHOSPHOROIMIDOPHENYL INSECTICIDES

[75] Inventor: Arnold D. Gutman, Berkeley, Calif.

[73] Assignee: Stauffer Chemical Company, Westport, Conn.

[21] Appl. No.: 668,341

[22] Filed: Mar. 18, 1976

Related U.S. Application Data

[63] Continuation-in-part of Ser. No. 635,556, Nov. 22, 1975, abandoned.

[51] Int. Cl.² .......................... A01N 9/36; C07F 9/24; C07F 9/44
[52] U.S. Cl. ..................................... 424/212; 260/941; 260/944; 260/945; 260/949; 260/950; 260/951; 424/211; 424/216; 424/217
[58] Field of Search .............. 260/941, 944, 945, 950, 260/951, 949; 424/211, 212, 216, 217

[56] References Cited

U.S. PATENT DOCUMENTS

| | | | |
|---|---|---|---|
| 3,882,103 | 5/1975 | Beriger et al. | 260/945 X |
| 3,888,951 | 6/1975 | Hoffmann et al. | 260/945 |
| 3,922,324 | 11/1975 | Hoffmann et al. | 260/950 |
| 3,975,523 | 8/1976 | Hoffmann | 260/941 X |

FOREIGN PATENT DOCUMENTS 1223381  8/1966  Fed. Rep. of Germany .

*Primary Examiner*—Richard Raymond
*Attorney, Agent, or Firm*—M. Henry Heines; Daniel C. Block

[57] ABSTRACT

Insecticidally active compounds are described herein, which are defined by the following generic formula

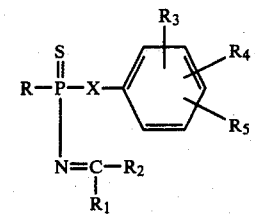

wherein
  X is oxygen or sulfur;
  R is lower alkyl or lower alkoxy;
  $R_1$ is hydrogen or lower alkyl;
  $R_2$ is selected from the group consisting of lower alkoxy, $NH_2$, $NHCH_3$, $N(CH_3)_2$,

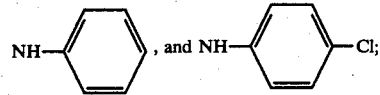

$R_3$ is selected from the group consisting of methyl, methoxy, $SCH_3$, $NO_2$, and

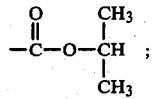

$R_4$ is selected from the group consisting of hydrogen, chlorine, and methyl; and
  $R_5$ is hydrogen or chlorine.

42 Claims, No Drawings

PHOSPHOROIMIDOPHENYL INSECTICIDES

CROSS REFERENCE TO RELATED APPLICATION

This application is a continuation-in-part of copending application Ser. No. 635,556, filed Nov. 22, 1975, now abandoned.

BACKGROUND OF THE INVENTION

Various substituted amidothionophosphorus compounds are known to be useful as insecticides and acaricides. Typical insecticidal properties of such compounds are taught in Belgian Patent No. 724,681. In particular, it is known from U.S. Pat. No. 3,922,324, that certain O-aryl-thionoalkanephosphonic acid ester-formamidines or imino-ethers, in which the aryl group is an optionally halogen-substituted phenyl group, have pesticidal activity.

BRIEF DESCRIPTION OF THE INVENTION

The present invention relates to a novel class of phosphoroimidophenyl compounds and to their use as insecticides when used in an insecticidally effective amount. More specifically, this invention relates to compounds having the formula

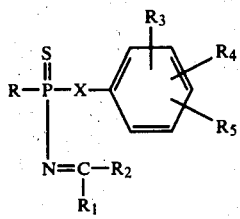

wherein
X is oxygen or sulfur;
R is lower alkyl or lower alkoxy;
$R_1$ is hydrogen or lower alkyl;
$R_2$ is selected from the group consisting of lower alkoxy, $NH_2$, $NHCH_3$, $N(CH_3)_2$,

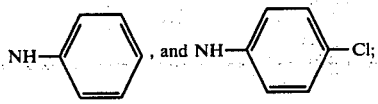

$R_3$ is selected from the group consisting of methyl, methoxy, $SCH_3$, $NO_2$, and

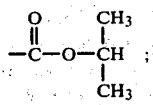

$R_4$ is selected from the group consisting of hydrogen, chlorine, and methyl; and
$R_5$ is hydrogen or chlorine.

By "lower alkyl" is meant straight- or branched-chain alkyl groups containing from one to four carbon atoms, inclusive. By "lower alkoxy" is meant straight- or branched-chain alkoxy groups having from one to four carton atoms, inclusive.

By "insecticidally effective amount" is meant the amount of the herein disclosed insecticidal compounds which when applied to the habitat of insects in any conventional manner will kill or substantially injure a significant portion of the population thereon.

DETAILED DESCRIPTION OF THE INVENTION

The following general method of preparation can be used to prepare any of the compounds of the present invention: A phenol is reacted with a dichlorophosphorus compound in the presence of a base to produce a phenoxyphosphorus chloride. The phenoxyphosphorus chloride is then reacted with ammonia to produce the amidate and with an ortho ester in the presence of an acid catalyst to produce the desired imidate. The imidate can be reacted further with an amine to produce the desired amidine.

The examples shown herein are illustrative of the method of preparation described hereinabove. The compound numbers refer to Table I which is a further listing of compounds which are representative of those embodied in the present invention. The additional compounds in Table I can be prepared in a manner analogous to that shown for the compounds in the examples, when the appropriate starting materials are used.

Example I

O-(3-methyl-4-nitrophenyl)-N-(α-ethoxyacetylidene)ethylthiophosphonamidate (Compound No. 2)

45.9 g (0.3 mole) of 3-methyl-4-nitrophenol, 65 g (0.3 mole) of 25% sodium methoxide solution, 54 g (0.33 mole) of ethylthiophosphonodichloride, and 500 ml of tetrahydrofuran were combined to yield 70 g of O-(3-methyl-4-nitrophenyl) ethylthiophosphonochloridate, not distillable at 140°/0.01 mm. The chloridate was then combined with 400 ml of diethylether and an excess of ammonia gas to yield 57 g of O-(3-methyl-4-nitrophenyl)ethylthiophosphonamidate, $n_D^{30} = 1.5932$, structure confirmed by NMR. 5.2 g (0.02 mole of this product, 8.1 g (0.05 mole) of triethylorthoacetate, 0.5 ml of alcoholic HCl, and 50 ml of acetonitrile were then combined to yield 6.5 g of O-(3-methyl-4-nitrophenyl)-N-(α-ethoxyacetylidene)ethylthiophosphonoamidate, $n_D^{30} = 1.53735$.

EXAMPLE II

N-[O-(3-methyl-4-nitrophenyl)ethylphosphonothioyl]formamidine (Compound No. 8)

In a manner similar to Example I above, O-(3-methyl-4-nitrophenyl)N-(methoxyformylidene)ethylthiophosphonamidate was prepared. 5 g (0.0165 mole) of this compound dissolved in 5 ml of ethanol was cooled in an ice bath. Ammonia gas was slowly bubbled through the solution while the reaction temperature was maintained below 40° C. When an exotherm could no longer be detected, the mixture was stripped in vacuo to yield 4.6 g of N-[O-(3-methyl-4-nitrophenyl)ethylphosphonothioyl]formamidine, $n_D^{30} = 1.5710$.

EXAMPLE III

N-[O-(2,4-dichloro-5-methylphenyl)ethylphosphonothioyl]-N'-phenylformamidine (Compound No. 17)

In a 500 ml round bottom flask, equimolar amounts of 2,4-dichloro-5-methylphenol and a 25% sodium methoxide solution were combined and heated under reflux for 15 minutes. The solution was then stripped in vacuo. To the residue was added 250 ml of benzene and the mixture was again stripped in vacuo. The solid residue was dissolved in 200 ml of tetrahydrofuran and the solution was added through a dropping funnel to a stirring solution of 32.6 (0.2 mole) ethylthiophosphonodichloride in 100 ml of tetrahydrofuran. The addition was carried out over a period of 30 minutes at a temperature of 10° C. After the addition was complete, the mixture was stirred at room temperature for 2 hours, then poured into 400 ml of benzene. THe benzene mixture was washed with two 300 ml portions of ice water, then dried with MgSO4. The benzene was removed in vacuo. The residue was distilled at reduced pressure to yield (O-(2,4-dichloro-5-methylphenyl)-N-(methoxyformylidene)ethylthiophosphonamidate. Five g (0.0154 mole) of this compound and 1.44 g (0.0154 mole) of aniline were combined. The reaction mass was heated on a steam bath for 1 hour, then stripped at 45°/100μ to yield 4.9 g of N-[O-(2,4-dichloro-5-methylphenyl)ethylphosphonothioyl]-N-phenylformamidine, $n_D^{30}$ 32 1.6010.

EXAMPLE IV

N-[O-(2,4-dichloro-5-methylphenyl)ethylphosphonothioyl]-N'-(4-chlorophenyl)formamidine (Compound No. 18)

Five g (0.0154 mole) of O-(2,4-dichloro-5-methylphenyl)-N-(methoxyformylidene)ethylthiophosphonamidate, as prepared in Example III, and 1.97 g (0.0154 mole) of 4-chloroaniline were combined to yield 6.0 g of N-[O-(2,4-dichloro-5-methylphenyl)ethylphosphonothioyl]-N'-(4-chlorophenyl)formamidine, $n_D^{30} = 1.6092$.

The compounds in the examples hereinabove are listed in Table I together with other compounds which are representative of the types of compounds embodied in the present invention. The methods of preparation for these compounds and those of the entire genus of which they are representative are analogous to those exemplified in the examples hereinabove, when the appropriate starting materials are used.

TABLE I

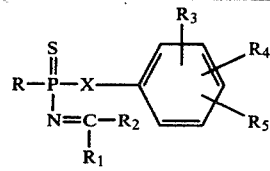

| Compound No. | R | $R_1$ | $R_2$ | $R_3$ | $R_4$ | $R_5$ | X | $n_D^{30}$ or m.p. |
|---|---|---|---|---|---|---|---|---|
| 1 | C2H5 | H | OC2H5 | 4-NO2 | 3-CH3 | H | O | 1.5644 |
| 2 | C2H5 | CH3 | OC2H5 | 4-NO2 | 3-CH3 | H | O | 1.5375 |
| 3 | C2H5 | H | OC2H5 | 2-CO2CH(CH3)2 | H | H | O | 1.5245 |
| 4 | C2H5 | CH3 | OC2H5 | 2-CO2CH(CH3)2 | H | H | O | 1.5300 |
| 5 | C2H5 | H | OCH3 | 2-CO2CH(CH3)2 | H | H | O | 1.5333 |
| 6 | C2H5 | H | NH2 | 2-CO2CH(CH3)2 | H | H | O | 143°–144° C. |
| 7 | C2H5 | H | NHCH3 | 4-NO2 | 3-CH3 | H | O | 1.5840 |
| 8 | C2H5 | H | NH2 | 4-NO2 | 3-CH3 | H | O | 1.5710 |
| 9 | C2H5 | H | OCH3 | 4-NO2 | H | H | O | 110°–112° C. |
| 10 | C2H5 | CH3 | OC2H5 | 4-NO2 | H | H | O | 108°–110° C. |
| 11 | C2H5 | H | OCH3 | 5-CH3 | 4-Cl | 2-Cl | O | 1.5655 |
| 12 | C2H5 | H | OC2H5 | 5-CH3 | 4-Cl | 2-Cl | O | 1.5421 |
| 13 | C2H5 | CH3 | OC2H5 | 5-CH3 | 4-Cl | 2-Cl | O | 1.4840 |
| 14 | C2H5 | C2H5 | OC2H5 | 5-CH3 | 4-Cl | 2-Cl | O | 1.5370 |
| 15 | C2H5 | CH3 | NHCH3 | 5-CH3 | 4-Cl | 2-Cl | O | 1.5700 |
| 16 | C2H5 | H | NHCH3 | 5-CH3 | 4-Cl | 2-Cl | O | 1.5845 |
| 17 | C2H5 | H | —NH—⟨phenyl⟩ | 5-CH3 | 4-Cl | 2-Cl | O | 1.6010 |
| 18 | C2H5 | H | —NH—⟨phenyl⟩—Cl | 5-CH3 | 4-Cl | 2-Cl | O | 1.6092 |
| 19 | C2H5 | H | OCH3 | 4-SCH3 | H | H | O | 1.5873 |
| 20 | C2H5 | H | OC2H5 | 4-SCH3 | H | H | O | 1.5145 |
| 21 | C2H5 | CH3 | OC2H5 | 4-SCH3 | H | H | O | 1.5013 |
| 22 | C2H5 | C2H5 | OC2H5 | 4-SCH3 | H | H | O | 1.5645 |
| 23 | C2H5 | H | NH2 | 4-SCH3 | H | H | O | 1.5563 |
| 24 | C2H5 | H | N(CH3)2 | 4-SCH3 | H | H | O | 1.5439 |
| 25 | C2H5 | H | NHCH3 | 4-SCH3 | H | H | O | 1.5790 |
| 26 | C2H5 | CH3 | N(CH3)2 | 4-SCH3 | H | H | O | 1.5428 |
| 27 | C2H5 | H | OCH3 | 4-OCH3 | H | H | O | 1.5459 |
| 28 | C2H5 | CH3 | NHCH3 | 4-SCH3 | H | H | O | 1.5400 |

Insecticide Evaluation

A. Housefly (*Musca domestica* L.)

Test compounds are diluted in acetone and aliquots are pipetted onto the bottom of 55×15 mm aluminum dishes. To insure even spreading of the chemical on the bottom of the dishes, one ml of acetone containing 0.02% peanut oil is also added to each dish. After all solvents have evaporated the dishes are placed in circular cardboard cages containing 25 three-day-old female houseflies. The cages are covered on the bottom with cellophane and the top with tulle netting, and each contains a sugar-water saturated cotton plug for maintenance of the flies. Mortality is recorded after 48 hours. Test levels range from 100 ug/25 ♀ houseflies down to that at which approximately 50% mortality occurs.

B. German Cockroach [*Blattella germanica* (Linne)]

Test compounds are diluted in a 50—50 acetone-water solution. Two cc of the solutions are sprayed through a DeVilbiss type EGA hand spray gun into circular cardboard cages containing ten one-month-old German cockroach nymphs. The test cages are covered on the bottom with cellophane and the top with tulle netting. Percent mortality is recorded 7 days later. Test concentrations range from 0.1% down to that at which approximately 50% mortality occurs.

C. Lygus Bug [*Lygus hesperus* (Knight)]

Test compounds are in a 50—50 acetone-water solution. Two cc of the solutions are sprayed through a DeVilbiss type EGA hand spray gun into circular cardboard cages containing one string bean pod and ten adult lygus bugs. The test cages are covered on the bottom with cellophane and the top with tulle netting. Percent mortality is recorded 48 hours later. Test concentrations range from 0.05% down to that at which approximately 50% mortality occurs.

D. Direct Spray Assay on Black Bean Aphid [*Aphis fabae* (Scop.)]

Nasturtium plants (*Tropaeolum sp.*), approximately 5 cm tall, are transplanted into sandy loam soil in 3-inch clay pots and infested with 25-50 black bean aphids of mixed ages. Twenty-four hours later they are sprayed, to the point of runoff, with 50—50 acetone-water solutions of the test chemicals. Treated plants are held in the greenhouse and mortality is recorded after 7 days. Test concentrations range from 0.05% down to that at which 50% mortality occurs.

E. Systemic Assay on Black Bean Aphid [*Aphis fabae* (Scop.)]

Test chemicals are diluted in acetone and aliquots are thoroughly mixed into 500 grams of dry, sandy loam soil. The treated soil is placed in a pint ice cream carton and a nasturtium plant (*Tropaeolum sp.*) approximately 5 cm tall is transplanted into each carton. The plants are then infested with approximately 25 black bean aphids of mixed ages and placed in the greenhouse. Seven days later mortality is recorded, and plants which show 100% mortality at 1 PPM are reinfested with aphids. This procedure is repeated weekly until all control is lost. Test concentrations range from 10 PPM down to that at which approximately 50% mortality occurs.

F. Salt-Marsh Caterpillar [*Estigmene acrea* (Drury)]

Test compounds are diluted in a 50—50 acetone-water solution. Sections of curly dock (*Rumex crispus*) leaves, approximately 1×1.5 inches, are immersed in the test solutions for 2-3 seconds and placed on a wire screen to dry. The dried leaves are placed in petri dishes containing a moistened piece of filter paper and infested with five second-instar salt-marsh larvae. Mortality of the larvae is recorded 48 hours later, and a piece of synthetic media is added to dishes containing survivors. These are then held for five additional days to observe for any delayed effects of the test chemicals. Test concentrations range from 0.05% down to that at which approximately 50% mortality occurs.

G. Beet Armyworm [*Spodoptera exigua* (Hubner)]

Test compounds are diluted in a 50—50 acetone-water solution. Sections of Romaine lettuce (*Latuca sativa*) leaves, approximately 1×1.5 inches, are immersed in the test solutions for 2-3 seconds and placed on a wire screen to dry. The dried leaves are placed in petri dishes containing a moistened piece of filter paper and infested with five second-instar been armyworm larvae. Mortality of the larvae is recorded 48 hours later, and a piece of synthetic media is added to dishes containing survivors. These are then held for five additional days to observe for any delayed effects of the test chemicals. Test concentrations range from 0.1% down to that at which approximately 50% mortality occurs.

H. Tobacco Budworm [*Heliothis virescens* (F.)]

The procedure is the same as that used for the beet armyworm.

I. Southern House Mosquito

Insecticidal activity is determined using third-instar larvae of the mosquito (*Culex pipiens quinquefasciatus*). Ten larvae are placed in a six-ounce, number 67 Dixie wax paper cup containing 100 ml of an aqueous solution of the test chemical. The treated larvae are stored at 70° F., and 48 hours later the mortality is recorded. Test concentrations range from 0.5 PPM down to that at which approximately 50% mortality occurs.

J. Soil Insecticide Assay on Larvae of the Housefly (*Musca domestica* L.)

Test compounds are diluted in acetone and aliquots are thoroughly incorporated into 250 grams of moist sandy loam soil. Twenty-five five-day-old housefly larvae are introduced into the treated soil. Forthy-eight hours later the larvae and/or pupae are retrieved from the soil, placed on a piece of moist filter paper in a petri dish, and held until the adult flies have emerged from the pupal cases. Mortality is determined by the percentage of adult flies failing to emerge. Test concentrations range from 10 PPM in the soil down to that at which 50% mortality occurs.

K. Plant Dip Assay on Two-Spotted Mite

Pinto bean plants (*Phaseolus* sp.) approximately 10 cm tall, are transplanted into sandy loam soil in 3-inch clay pots and thoroughly infested with two-spotted mites of mixed ages and sexes. Twenty-four hours later the infested plants are inverted and dipped for 2-3 seconds in 50—50 acetone-water solution of the test chemicals. Treated plants are held in the greenhouse, and seven days later mortality is determined for both the adult mites and the nymphs hatching from eggs which were on the plants at the time of treatment. Test concentrations range from 0.05% down to that at which 50% mortality occurs.

L. Systemic Assay on Two-Spotted Mite

Test chemicals are dissolved in acetone and aliquots are diluted in 200 cc of water in glass bottles. Two pinto bean plants (*Phaseolus* sp.), with expanded primary leaves, are supported in each bottle by cotton plugs, so that their roots and stems are immersed in the treated water. The plants are then infested with 75-100 two-spotted mites of various ages and sexes. One week later the mortality of the adult mites and nymphs is recorded. Test concentrations range from 10 PPM down to that at which 50% mortality occurs.

The results of these tests on the compounds listed in Table I are shown in Table II below.

TABLE II

Insecticide Activity - Approximate LD$_{50}$ Values

| Compound Number | HF μg/25 ♀ | GR % | LB % | BA % | BAS ppm | SMC % | BAW % | TBW % | MOS ppm | HF-SOIL ppm | 2SM PE % | 2SM EGGS % | 2SM SYS ppm |
|---|---|---|---|---|---|---|---|---|---|---|---|---|---|
| 1 | 5 | .008 | .003 | .001 | 10 | .01 | .03 | .03 | .08 | 1 | <.05 | <.05 | >10 |
| 2 | 9 | .005 | .008 | .003 | 8 | .01 | .05 | .05 | .3 | 3 | <.05 | <.05 | >10 |
| 3 | 30 | .01 | .01 | .0003 | >.05 | >.05 | .1 | .1 | .5 | >10 | <.05 | <.05 | 3 |
| 4 | 30 | .01 | .03 | .03 | 3 | >.05 | .05 | .05 | >.5 | >10 | <.05 | <.05 | 8 |
| 5 | 30 | >.1 | .05 | .001 | — | >.05 | >.1 | .08 | >.5 | >10 | <.05 | <.05 | 8 |
| 6 | >100 | — | — | .03 | — | >.05 | — | — | >.5 | — | <.05 | >.05 | 10 |
| 7 | 30 | >.1 | >.05 | .03 | >10 | >.05 | .1 | >.1 | >.5 | >10 | <.05 | <.05 | >10 |
| 8 | 6 | .03 | .01 | .008 | >10 | >.1 | .1 | .1 | .3 | >10 | <.05 | <.05 | 10 |
| 9 | 20 | .03 | .008 | .01 | >10 | >.1 | >.1 | >.1 | .4 | >10 | <.05 | <.05 | >10 |
| 10 | 15 | >.1 | >.05 | .008 | >10 | >.1 | >.1 | >.1 | .4 | >10 | <.05 | <.05 | >10 |
| 11 | 20 | .03 | .03 | .003 | >10 | >.1 | >.1 | >.1 | >.5 | 8 | .05 | <.05 | >10 |
| 12 | 10 | >.1 | .01 | .003 | >10 | >.05 | .05 | .05 | >.5 | >10 | >.05 | <.05 | — |
| 13 | 20 | .03 | >.05 | .003 | >10 | .05 | >.1 | — | >.5 | 3 | <.05 | <.05 | >10 |
| 14 | 80 | .1 | .05 | .003 | >10 | .03 | >.1 | — | >.5 | >10 | <.05 | <.05 | >10 |
| 15 | 90 | >.1 | .05 | .05 | >10 | >.05 | >.1 | — | >.5 | >10 | <.05 | <.05 | >10 |
| 16 | 20 | .05 | >.01 | .001 | 3 | >.05 | >.1 | — | .3 | 8 | <.05 | <.05 | >10 |
| 17 | 20 | >.1 | .05 | .003 | 3 | >.05 | >.1 | — | .5 | 3 | <.05 | <.05 | >10 |
| 18 | 20 | >.1 | .05 | .003 | >10 | .05 | >.1 | — | .5 | >10 | <.05 | <.05 | >10 |
| 19 | 8 | .01 | .001 | .003 | 3 | >.1 | — | >.1 | .05 | — | <.05 | <.05 | 3 |
| 20 | 20 | .03 | .003 | .0005 | 1 | >.1 | — | >.1 | .07 | — | <.05 | <.05 | 3 |
| 21 | 8 | .01 | .005 | .0001 | 3 | >.05 | — | .1 | .008 | — | <.05 | <.05 | 3 |
| 22 | 10 | .01 | .005 | .0001 | .8 | >.05 | — | — | .008 | — | <.05 | <.05 | 1 |
| 23 | 9 | .05 | .003 | .003 | 3 | >.05 | — | >.1 | .08 | — | <.05 | <.05 | 3 |
| 24 | 15 | .03 | .003 | .0001 | .8 | >.05 | — | >.1 | .03 | — | — | — | 5 |
| 25 | 9 | .03 | .001 | .0003 | 3 | >.05 | — | >.1 | — | — | <.05 | <.05 | — |
| 26 | 20 | .08 | .005 | .0003 | 3 | >.05 | — | >.1 | .03 | — | <.05 | <.05 | 5 |
| 27 | 20 | >.1 | .05 | .03 | >10 | >.05 | — | >.1 | >.5 | — | .05 | <.05 | >10 |
| 28 | 20 | >.1 | .005 | .0003 | — | >.05 | — | — | .3 | — | <.05 | <.05 | 3 |

HF: Housefly - contact residue
GR: German Cockroach
LB: Lygus Bug
BA: Black Bean Aphid - direct spray
BAS: Black Bean Aphid - systemic
SMC: Salt-marsh Caterpillar
BAW: Beet Armyworm
TBW: Tobacco Budworm
MOS: Southern House Mosquito
HF-Soil: Housefly larvae - soil insecticide
2SM: Two-Spotted Mite
PE: Post-emergence
EGGS: Eggs
SYS: Systemic The compositions of this invention are generally embodied in formulations suitable for convenient application. In general, such formulations will contain inert or occasionally active ingredients or diluent carriers in addition to the active compound. Examples of such ingredients or carriers are organic solvents, such as sesame oil, xylene range solvents, and heavy petroleum; water; emulsifying agents; surface active agents; talc; pyrophyllite; diatomite; gypsum; clays; and propellants, such as dichlorodifluoromethane.

The active compositions can be combined with dust carriers for application as dusts, with granular carriers for application by fertilizer spreaders or ground or airplane seeders, with wettable powders or flowable carriers for application as water suspensions, and with solvents and surface active materials for application as sprays, aerosols, or emulsions. The compositions can be applied to any habitat of the pests, for example, dwellings, clothing, plant and insect surfaces, soil, etc. If desired, however, the active compositions can be applied directly to feedstuffs, seeds, etc., upon which the pests feed. When applied in such a manner, it will be advantageous to use a composition which is not volatile.

The amount of active composition or formulation which is considered to be insecticidally effective is that amount which, when applied to the pest habitat, will kill or substantially injure a significant portion residing thereon. The active compounds of this invention can be employed either as the sole pesticide component of the formulation or as one of a mixture of compounds in the formulation having similar utility. Furthermore, the presently disclosed pesticide compositions need not be active as such. The purposes of this invention will be fully served by a composition which is rendered active by external influences, such as light, or by some physiological action which occurs when the preparation is ingested or penetrates into the body of the pest.

The precise manner in which the pesticide compositions of this invention are used in any particular instance will be readily apparent to a person skilled in the art. Generally, the active pesticidal composition will be embodied in the form of a liquid composition; for example, an emulsion, suspension, or aerosol spray. While the concentration of the active pesticide composition in the present forumlation can vary within rather wide limits, ordinarily, the pesticide composition will comprise not more than about 50.0% by weight of the formulation.

What is claimed is:

1. A compound having the formula

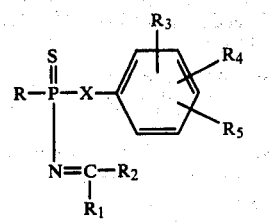

wherein
X is oxygen or sulfur;
R is alkyl or alkoxy having from one to four carbon atoms, inclusive;
$R_1$ is hydrogen or alkyl having from one to four carbon atoms, inclusive;
$R_2$ is alkoxy having from one to four carbon atoms, inclusive;
$R_3$ is selected from the group consisting of methoxy, $SCH_3$, $NO_2$, and

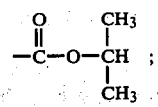

$R_4$ is selected from the group consisting of hydrogen, chlorine, and methyl; and
$R_5$ is hydrogen or chlorine.

2. A compound according to claim 1 wherein R is $C_2H_5$, $R_1$ is H, $R_2$ is $OC_2H_5$, $R_3$ is 4-$NO_2$, $R_4$ is 3-$CH_3$, $R_5$ is H, and X is O.

3. A compound according to claim 1 wherein R is $C_2H_5$, $R_1$ is $CH_3$, $R_2$ is $OC_2H_5$, $R_3$ is 4-$NO_2$, $R_4$ is 3-$CH_3$, $R_5$ is H, and X is O.

4. A compound according to claim 1 wherein R is $C_2H_5$, $R_1$ is H, $R_2$ is $OC_2H_5$, $R_3$ is 2-$CO_2CH(CH_3)_2$, $R_4$ is H, $R_5$ is H and X is O.

5. A compound according to claim 1 wherein R is $C_2H_5$, $R_1$ is $CH_3$, $R_2$ is $OC_2H_5$, $R_3$ is 2-$CO_2CH(CH_3)_2$, $R_4$ is H, $R_5$ is H, and X is O.

6. A compound according to claim 1 wherein R is $C_2H_5$, $R_1$ is H, $R_2$ is $OCH_3$, $R_3$ is 2-$CO_2CH(CH_3)_2$, $R_4$ is H, $R_5$ is H, and X is O.

7. A compound according to claim 1 wherein R is $C_2H_5$, $R_1$ is H, $R_2$ is $OCH_3$, $R_3$ is 4-$NO_2$, $R_4$ is H, $R_5$ is H, and X is O.

8. A compound according to claim 1 wherein R is $C_2H_5$, $R_1$ is $CH_3$, $R_2$ is $OC_2H_5$, $R_3$ is 4-$NO_2$, $R_4$ is H, $R_5$ is H, and X is O.

9. A compound according to claim 1 wherein R is $C_2H_5$, $R_1$ is H, $R_2$ is $OC_2H_5$, $R_3$ is 4-$SCH_3$, $R_4$ is H, $R_5$ is H, and X is O.

10. A compound according to claim 1 wherein R is $C_2H_5$, $R_1$ is H, $R_2$ is $OC_2H_5$, $R_3$ is 4-$SCH_3$, $R_4$ is H, $R_5$ is H, and X is O.

11. A compound according to claim 1 wherein R is $C_2H_5$, $R_1$ is $CH_3$, $R_2$ is $OC_2H_5$, $R_3$ is 4-$SCH_3$, $R_4$ is H, $R_5$ is H, and X is O.

12. A compound according to claim 1 wherein R is $C_2H_5$, $R_1$ is $C_2H_5$, $R_2$ is $OC_2H_5$, $R_3$ is 4-$SCH_3$, $R_4$ is H, $R_5$ is H, and X is O.

13. A compound according to claim 1 wherein R is $C_2H_5$, $R_1$ is H, $R_2$ is $OCH_3$, $R_3$ is 4-$OCH_3$, $R_4$ is H, $R_5$ is H, and X is O.

14. An insecticidally active composition comprising an insecticidally effective amount of a compound having the formula

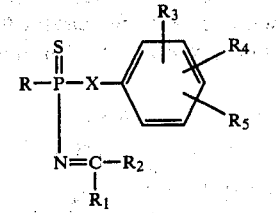

wherein X is oxygen or sulfur;
R is alkyl or alkoxy, having from one to four carbon atoms, inclusive;
$R_1$ is hydrogen or alkyl having from one to four carbon atoms, inclusive;
$R_2$ is alkoxy, having from one to four carbon atoms inclusive;
$R_3$ is selected from the group consisting of methoxy, $SCH_3$, $NO_2$, and

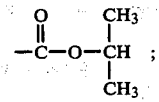

$R_4$ is selected from the group consisting of hydrogen, chlorine, and methyl; and
$R_5$ is hydrogen or chlorine;
and an inert diluent carrier.

15. A composition according to claim 14 wherein R is $C_2H_5$, $R_1$ is H, $R_2$ is $OC_2H_5$, $R_3$ is 4-$NO_2$, $R_4$ is 3-$CH_3$, $R_5$ is H, and X is O.

16. A composition according to claim 14 wherein R is $C_2H_5$, $R_1$ is $CH_3$, $R_2$ is $OC_2H_5$, $R_3$ is 4-$NO_2$, $R_4$ is 3-$CH_3$, $R_5$ is H, and X is O.

17. A composition according to claim 14 wherein R is $C_2H_5$, $R_1$ is H, $R_2$ is $OC_2H_5$, $R_3$ is 2-$CO_2CH(CH_3)_2$, $R_4$ is H, $R_5$ is H, and X is O.

18. A composition according to claim 14 wherein R is $C_2H_5$, $R_1$ is $CH_3$, $R_2$ is $OC_2H_5$, $R_3$ is 2-$CO_2CH(CH_3)_2$, $R_4$ is H, $R_5$ is H, and X is O.

19. A composition according to claim 14 wherein R is $C_2H_5$, $R_1$ is H, $R_2$ is $OCH_3$, $R_3$ is 2-$CO_2CH(CH_3)_2$, $R_4$ is H, $R_5$ is H, and X is O.

20. A composition according to claim 14 wherein R is $C_2H_5$, $R_1$ is H, $R_2$ is $OCH_3$, $R_3$ is 4-$NO_2$, $R_4$ is H, $R_5$ is H, and X is 0.

21. A composition according to claim 14 wherein R is $C_2H_5$, $R_1$ is $CH_3$, $R_2$ is $OC_2H_5$, $R_3$ is 4-$NO_2$, $R_4$ is H, $R_5$ is H, and X is O.

22. A composition according to claim 14 wherein R is $C_2H_5$, $R_1$ is H, $R_2$ is $OC_2H_5$, $R_3$ is 4-$SCH_3$, $R_4$ is H, $R_5$ is H, and X is O.

23. A composition according to claim 14 wherein R is $C_2H_5$, $R_1$ is H, $R_2$ is $OC_2H_5$, $R_3$ is 4-$SCH_3$, $R_4$ is H, $R_5$ is H, and X is O.

24. A composition according to claim 14 wherein R is $C_2H_5$, $R_1$ is $CH_3$, $R_2$ is $OC_2H_5$, $R_3$ is 4-$SCH_3$, $R_4$ is H, $R_5$ is H, and X is O.

25. A composition according to claim 14 wherein R is $C_2H_5$, $R_1$ is $C_2H_5$, $R_2$ is $OC_2H_5$, $R_3$ is 4-$SCH_3$, $R_4$ is H, $R_5$ is H, and X is O.

26. A composition according to claim 14 wherein R is $C_2H_5$, $R_1$ is H, $R_2$ is $OCH_3$, $R_3$ is 4-$OCH_3$, $R_4$ is H, $R_5$ is H, and X is O.

27. A method of controlling insects comprising applying to the habitat thereof an insecticidally effective amount of a compound having the formula

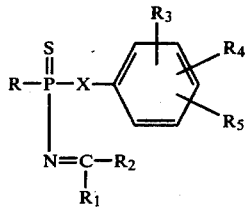

wherein
X is oxygen or sulfur;
R is alkyl or alkoxy, having from one to four carbon atoms, inclusive;
$R_1$ is hydrogen or alkyl having from one to four carbon atoms, inclusive;
$R_2$ is alkoxy having from one to four carbon atoms inclusive;
$R_3$ is selected from the group consisting of methoxy, $SCH_3$, $NO_2$, and

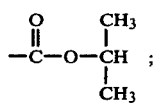

$R_4$ is selected from the group consisting of hydrogen, chlorine, and methyl; and
$R_5$ is hydrogen or chlorine;
and an inert diluent carrier.

28. A method according to claim 27 wherein R is $C_2H_5$, $R_1$ is H, $R_2$ is $OC_2H_5$, $R_3$ is 4-$NO_2$, $R_4$ is 3-$CH_3$, $R_5$ is H, and X is O.

29. A method according to claim 27 wherein R is $C_2H_5$, $R_1$ is $CH_3$, $R_2$ is $OC_2H_5$, $R_3$ is 4-$NO_2$, $R_4$ is 3-$CH_3$, $R_5$ is H, and X is O.

30. A method according to claim 27 wherein R is $C_2H_5$, $R_1$ is H, $R_2$ is $OC_2H_5$, $R_3$ is 2-$CO_2CH(CH_3)_2$, $R_4$ is H, $R_5$ is H, and X is O.

31. A method according to claim 27 wherein R is $C_2H_5$, $R_1$ is $CH_3$, $R_2$ is $OC_2H_5$, $R_3$ is 2-$CO_2CH(CH_3)_2$, $R_4$ is H, $R_5$ is H, and X is O.

32. A method according to claim 27 wherein R is $C_2H_5$, $R_1$ is H, $R_2$ is $OCH_3$, $R_3$ is 2-$CO_2CH(CH_3)_2$, $R_4$ is H, $R_5$ is H, and X is O.

33. A method according to claim 27 wherein R is $C_2H_5$, $R_1$ is H, $R_2$ is $OCH_3$, $R_3$ is 4-$NO_2$, $R_4$ is H, $R_5$ is H, and X is O.

34. A method according to claim 1 wherein R is $C_2H_5$, $R_1$ is $CH_3$, $R_2$ is $OC_2H_5$, $R_3$ is 4-$NO_2$, $R_4$ is H, $R_5$ is H, and X is O.

35. A method according to claim 27 wherein R is $C_2H_5$, $R_1$ is H, $R_2$ is $OC_2H_5$, $R_3$ is 4-$SCH_3$, $R_4$ is H, $R_5$ is H, and X is O.

36. A method according to claim 27 wherein R is $C_2H_5$, $R_1$ is H, $R_2$ is $OC_2H_5$, $R_3$ is 4-$SCH_3$, $R_4$ is H, $R_5$ is H, and X is O.

37. A method according to claim 27 wherein R is $C_2H_5$, $R_1$ is $CH_3$, $R_2$ is $OC_2H_5$, $R_3$ is 4-$SCH_3$, $R_4$ is H, $R_5$ is H, and X is O.

38. A method according to claim 27 wherein R is $C_2H_5$, $R_1$ is $C_2H_5$, $R_2$ is $OC_2H_5$, $R_3$ is 4-$SCH_3$, $R_4$ is H, $R_5$ is H, and X is O.

39. A method according to claim 27 wherein R is $C_2H_5$, $R_1$ is H, $R_2$ is $OCH_3$, $R_3$ os 4-$OCH_3$, $R_4$ is H, $R_5$ is H, and X is O.

40. An O-(carbisopropoxyphenyl)-thionophosphoric (phosphonic) acid ester imide of the formula

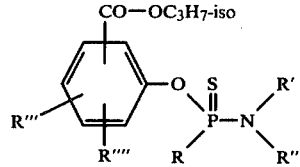

in which
R is alkyl or alkoxy of 1 to 4 carbon atoms,
R' and R'' conjointly form an alkoxymethylene radical, the alkoxy having 1 to 4 carbon atoms and the methylene being optionally substituted by an alkyl of 1 to 4 carbon atoms,
R''' is hydrogen, chlorine, or methyl, and
R'''' is hydrogen or chlorine.

41. An insecticidal composition containing as active ingredient an insecticidally effective amount of a compound according to claim 40 in admixture with a diluent.

42. A method of combatting insects which comprises applying to the insects or to a habitat thereof an insecticidally effective amount of a compound according to claim 40.

* * * * *